United States Patent
Ukil et al.

(10) Patent No.: US 10,206,593 B2
(45) Date of Patent: Feb. 19, 2019

(54) METHOD AND SYSTEM OF DETECTING ARRHYTHMIA USING PHOTOPLETHYSMOGRAM SIGNAL

(71) Applicant: Tata Consultancy Services Limited, Mumbai (IN)

(72) Inventors: Arijit Ukil, Kolkata (IN); Soma Bandyopadhyay, Kolkata (IN); Chetanya Puri, Kolkata (IN); Arpan Pal, Kolkata (IN); Kayapanda Mandana, Kolkata (IN)

(73) Assignee: Tata Consultancy Services Limited, Mumbai (IN)

(*) Notice: Subject to any disclaimer, the term of this patent is extended or adjusted under 35 U.S.C. 154(b) by 1 day.

(21) Appl. No.: 15/453,479

(22) Filed: Mar. 8, 2017

(65) Prior Publication Data
US 2017/0258342 A1 Sep. 14, 2017

(30) Foreign Application Priority Data
Mar. 14, 2016 (IN) .............................. 201621008876

(51) Int. Cl.
*A61B 5/024* (2006.01)
*A61B 5/00* (2006.01)

(52) U.S. Cl.
CPC .......... *A61B 5/02416* (2013.01); *A61B 5/725* (2013.01); *A61B 5/7221* (2013.01); *A61B 5/7264* (2013.01); *A61B 5/7275* (2013.01); *A61B 5/7282* (2013.01)

(58) Field of Classification Search
CPC ... A61B 5/6898; A61B 5/0077; A61B 5/0205; A61B 5/02427; A61B 5/02
USPC ............................................ 348/77; 600/508
See application file for complete search history.

(56) References Cited

U.S. PATENT DOCUMENTS

| 6,519,490 B1 | 2/2003 | Wiesel |
| 7,794,406 B2 | 9/2010 | Reisfeld et al. |
| 2006/0281998 A1 | 12/2006 | Li |
| 2010/0262025 A1 | 10/2010 | Hu et al. |
| 2013/0138002 A1 | 5/2013 | Weng et al. |
| 2015/0124067 A1* | 5/2015 | Bala ................... A61B 5/6898 348/77 |

FOREIGN PATENT DOCUMENTS

| WO | WO 2011/048592 A1 | 4/2011 |
| WO | WO 2012/166769 A1 | 12/2012 |

* cited by examiner

*Primary Examiner* — Carl H Layno
*Assistant Examiner* — Jon Eric C Morales
(74) *Attorney, Agent, or Firm* — Finnegan, Henderson, Farabow, Garrett & Dunner LLP

(57) ABSTRACT

A method and system of detecting arrhythmia using photoplethysmogram (PPG) signal is provided. The method is performed by extracting photoplethysmogram (PPG) signals from a patient, extracting cardiac parameter from the extracted photoplethysmogram (PPG) signals, identifying presence of cardiac abnormalities as reinforcement filtering of detecting premature ventricular contraction and ventricular flutter from the extracted cardiac parameters, analysing the extracted cardiac parameters to investigate statistical trend and to perform statistical closeness approximation of the extracted photoplethysmogram (PPG) signals and predicting and subsequently classifying type of arrhythmia.

14 Claims, 3 Drawing Sheets

METHOD AND SYSTEM OF DETECTING ARRHYTHMIA USING PHOTOPLETHYSMOGRAM SIGNAL

PRIORITY CLAIM

This U.S. patent application claims priority under 35 U.S.C. § 119 to: India Application No. 201621008876, filed on 14 Mar. 2016. The entire contents of the aforementioned application are incorporated herein by reference.

TECHNICAL FIELD

The present application generally relates to biomedical signal processing. More particularly, the application provides a method and system for detecting arrhythmia of a patient using photoplethysmogram (PPG) signal.

BACKGROUND

Huge number of IoT devices are available to promote health care management and wellness, like Blood Pressure monitor, Blood Glucose monitor, electroencephalogram (EEG) or brain signal monitor, pulse-oximeter, electrocardiogram (ECG) monitor, and many others. It is undoubted that IoT Healthcare solutions can provide remote monitoring to support patients suffering from various diseases and disorders. But, a gamut of expensive sensor devices, sophisticated, periodic setup, maintenance and calibration as well as up-to-date training are required for such purpose to come to fruition. In order to promote widespread usage and affordability, such costly and extensive intricacies do not work positively towards the ubiquity and success of mobile and preventable health care, specifically in developing countries. Cardiac problems, being fatal in nature, anytime, anywhere heart condition monitoring and alert generation scheme that detects fatal cardiac arrhythmia condition is highly necessary. So, affordable cardiac anomaly condition detection is of utmost importance. However, high false negative alarms would result in large amount of non-detection occurrences and high false alarms result alarm fatigue to the medical care giver as well as to the patients. It is a challenge to provide affordable yet accurate cardiac detection method. Smartphone, being ubiquitous in nature, smart phone based cardiac anomaly detection is useful for mass adoption.

Prior-arts deal with multiple physiological signal like PPG, ECG, ABP. For affordable and non-invasive method, only photoplethysmogram (PPG) signal is available for heart condition analysis. In all practicality, it is infeasible to capture ECG or ABP signals without using extra sensors or through invasive procedures. In a mobile or smart phone based application scenario, only PPG signal can be extracted without using additional sensors. Prior-arts use multi-signal analysis and, at the same time, prior art is rigid-analysis based. It detects heart condition based on static conditions. Thereby, assessing heart condition only through the analysis of PPG signals by using smartphones to detect arrhythmia with minimal false negatives is still considered to be one of the biggest challenges of the technical domain.

SUMMARY

Embodiments of the present disclosure present technological improvements as solutions to one or more of the above-mentioned technical problems recognized by the inventors in conventional systems. For example, in one embodiment, a method for detecting arrhythmia using photoplethysmogram (PPG) signal is provided. The method comprises extracting photoplethysmogram (PPG) signals from a patient, extracting cardiac parameter from the extracted photoplethysmogram (PPG) signals, identifying presence of cardiac abnormalities as reinforcement filtering of detecting premature ventricular contraction and ventricular flutter from the extracted cardiac parameters, analysing the extracted cardiac parameters to investigate statistical trend and to perform statistical closeness approximation of the extracted photoplethysmogram (PPG) signals and predicting and subsequently classifying type of arrhythmia.

In another embodiment, a system for detecting arrhythmia using photoplethysmogram (PPG) signal is provided. The system (200) comprises of an image capturing device (202) coupled with a mobile communication device (204), a feature extraction module (206), an abnormality detection module (208), a closeness criteria evaluation module (210) and a decision module (212).

In yet another embodiment, a non-transitory computer readable medium storing instructions which when executed by a possessor on a system, cause the processor to perform method for detecting arrhythmia using photoplethysmogram (PPG) signals is disclosed. The method comprises extracting photoplethysmogram (PPG) signals from a patient, extracting cardiac parameter from the extracted photoplethysmogram (PPG) signals, identifying presence of cardiac abnormalities as reinforcement filtering of detecting premature ventricular contraction and ventricular flutter from the extracted cardiac parameters, analysing the extracted cardiac parameters to investigate statistical trend and to perform statistical closeness approximation of the extracted photoplethysmogram (PPG) signals and predicting and subsequently classifying type of arrhythmia.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

The present disclosure provides a method and system for detecting arrhythmia using photoplethysmogram (PPG) signal of a patient.

Figure 1:
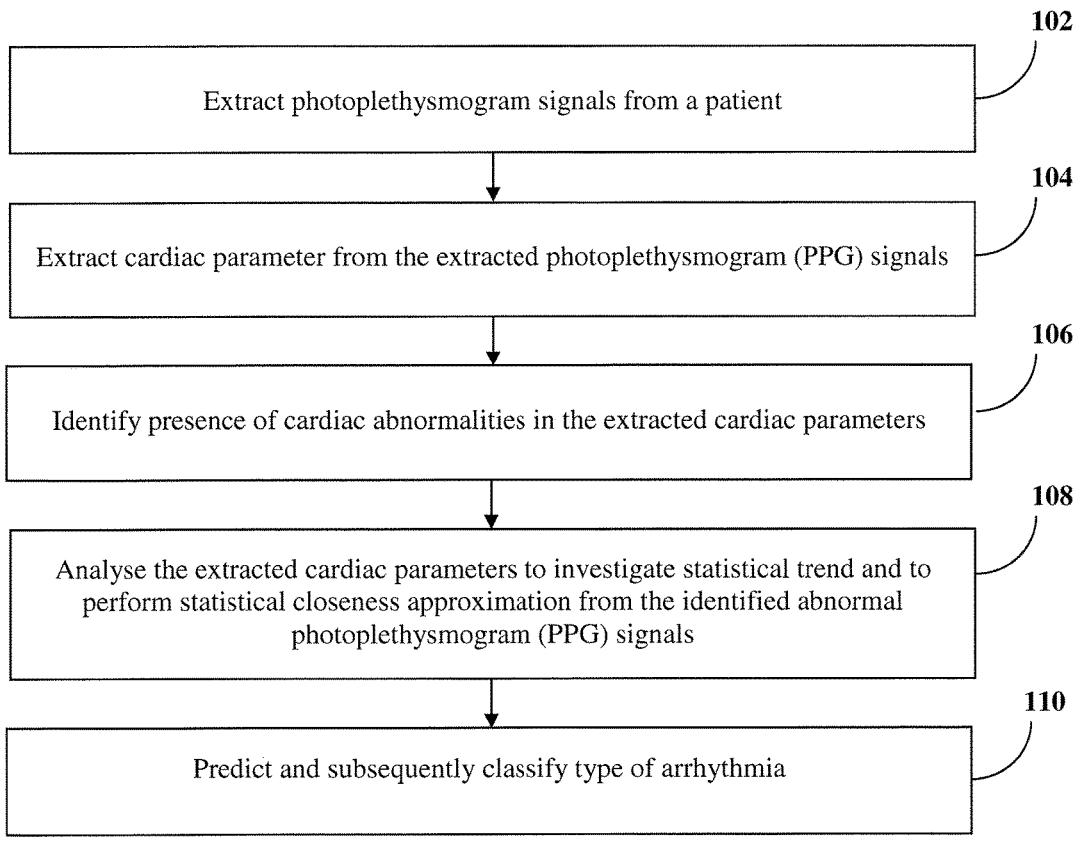
FIG. 1 shows a flow chart illustrating method for detecting arrhythmia using photoplethysmogram (PPG) signal.

Referring to FIG. 1, it is a flow chart illustrating a method for removing corruption in photoplethysmogram (PPG) signals for monitoring cardiac health of patients.

The process starts at step 102, photoplethysmogram signals are extracted from a patient using the image capturing device (202) coupled with the mobile communication device (204). At the step 104, cardiac parameters are extracted from the extracted photoplethysmogram (PPG) signals. At step 106, presence of cardiac abnormalities in the extracted cardiac parameters are identified. At step 108, the extracted cardiac parameters are analysed to investigate statistical trend and to perform statistical closeness approximation from the identified abnormal photoplethysmogram (PPG) signals and at step 110, type of arrhythmia is predicted and subsequently classified.

Figure 2:
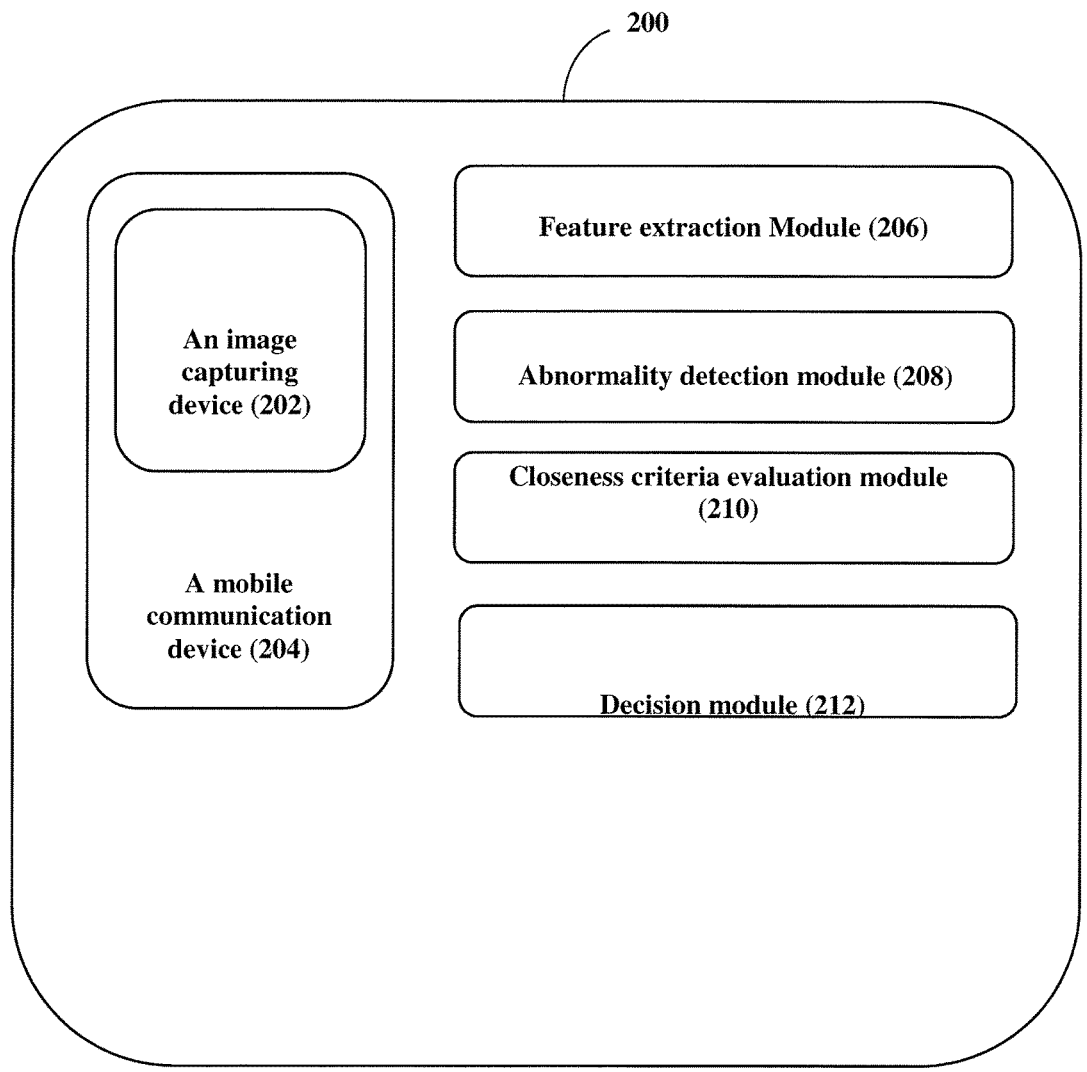
FIG. 2 shows a block diagram of a system for detecting arrhythmia using photoplethysmogram (PPG) signal.

Referring to FIG. 2, it is a block diagram illustrating system architecture for detecting arrhythmia using photoplethysmogram (PPG) signal of a patient.

In an embodiment of the present invention, a system (200) for detecting arrhythmia using photoplethysmogram (PPG) signal from patients comprises of an image capturing device (202) coupled with a mobile communication device (204), a feature extraction module (206), an abnormality detection module (208), a closeness criteria evaluation module (210) and a decision module (212).

In another embodiment of the present invention, the image capturing device (202) coupled with the mobile communication device (204) is adapted for extracting photoplethysmogram signals from the patient. The photoplethysmogram signals are extracted from patient's peripheral body parts selected from a group comprising but not limited to finger, ear, and toe. In a specific embodiment, the photoplethysmogram signals are extracted from user's forehead. The mobile communication device (204) captures photoplethysmogram signal in reflective mode. The mobile communication device (204) is selected from a group comprising of smart phone, mobile phone, laptop, tablet, and personal digital assistant.

The image capturing device (202) coupled with the mobile communication device (204) is a camera and have a light emitting source for extracting photoplethysmogram signals from the patient's peripheral body parts selected from a group comprising but not limited to finger, ear, toe; forehead, thereby, obtaining a video sequence of the light, reflected from patient's peripheral body parts.

In another embodiment of the present invention, the invention is a nonparametric, supervised statistical learning model to analyze and detect arrhythmia using only photoplethysmogram (PPG) signal. It does on-demand heart status monitoring and facilitates timely detection of heart condition deterioration to permit early diagnosis and prevention of fatal heart diseases. Proposed anomaly and trend analytics engine accurately detects the morphological trend through statistical learning through closeness function to find abnormal heart condition in real time. False negative detection rate is low while optimizing false positive rate, resulting in high clinical utility. It classifies abnormal heart condition like asystole, extreme bradycardia, extreme tachycardia, ventricular flutter and ventricular tachycardia to indicate the severity.

In another embodiment of the present invention, cardiac parameter is extracted by the feature extraction module (206) using a signal processing technique, wherein the extracted cardiac parameter is heart rate of a patient.

In another embodiment of the present invention, in the abnormality detection module (208), abnormal PPG signals are identified by using through Hurst exponent. Arrhythmia patients' heart condition is abnormal and consequently the PPG signal that originates from heart is also abnormal. Hurst exponent is a dimensionless estimator of time-series trend. Abnormal heart or equivalently PPG has inherent Brownian motion components, whereas normal PPG is anti-persistent. The following method is implemented to identify abnormal PPG signals as reinforcement filtering of detecting premature ventricular contraction and ventricular flutter:

a. Find Hurst exponent $\mathcal{H}$, as:

$$E\left[\frac{\mathcal{R}(n)}{\mathcal{C}(n)}\right] = \mathcal{X}n^{\mathcal{H}}, n \to \infty.$$

PPG signal $P=\{p_n\}$, of length N is divided into shorter time series of length n, where $$n = N, \frac{N}{2}, \frac{N}{4}, \ldots ..$$

The mean rescaled range is computed for each value of n and $\mathcal{R}(n)$ is the range of the first n values, and $\mathcal{C}(n)$ is corresponding standard deviation, $E[\cdot]$ is the expectation function.

b.

$$\mathcal{H} = \begin{cases} \geq 0.5, \text{Brownian motion} \to \text{abnormal } PPG \\ < 0.5, \text{Anti-persistent} \to \text{normal } PPG \end{cases}$$

Figure 3:
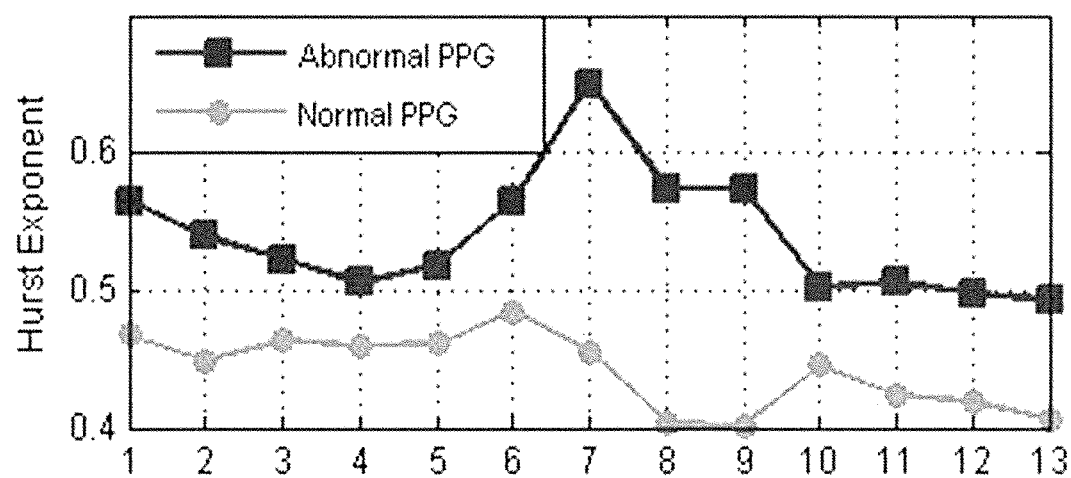
FIG. 3 illustrates heart abnormality indication using Hurst exponent.

In an exemplary embodiment of the present invention, 13 PPG signals of reported arrhythmia patients and 13 PPG signals of reported normal patients are considered randomly and it is clearly visible from FIG. 3 that patients with abnormal heart condition is reflected with Brownian motion ($\mathcal{H} \geq 0.5$) and normal condition shows anti-persistency ($\mathcal{H} < 0.5$).

In another embodiment of the present invention, in the closeness criteria evaluation module (210), the extracted cardiac parameters are analysed to investigate statistical trend and to perform closeness approximation from the identified abnormal photoplethysmogram (PPG) signals. Then, the type of arrhythmia is predicted as per severity indication of the type of arrhythmia.

In another embodiment of the present invention, the following method is implemented to determine the detection of extreme tachycardia and bradycardia:

c. Find the train of heart rates at each valid cardiac cycle for the given PPG signal, which is computed as:

$$\Psi = \{\Psi_k\} = \frac{1}{(\max(o_{k-1}:o_k) - \max(o_k:o_{k+1}))},$$

$\forall k \in (K-2)$, where $\psi_k$=Peak-to-peak duration at the cardiac cycle d. Find feature vector $\tau=\{\tau|_{brady}, \tau|_{normal}, \tau|_{tachy},\}$ from mean HR values ($\overline{\psi_{brady}}, \overline{\psi_{normal}}, \overline{\psi_{tachy}}$) random bradycardia, normal, tachycardia patients respectively. This feature vector is generic enough, we can include other heart anomaly condition features as well. The arrhythmia conditions are exemplary, included without loss of generality.

a. Find the classification outcome set a from the heart rate series $\psi$, which is closest to $\tau$ for each case of bradycardia, normal and tachycardia using k-nn classifier. i.e. to generate $\sigma_{brady}, \sigma_{normal}, \sigma_{tachy}$.

b. Classify $\sigma$ to one of the three classes using binary classifier k-means (k=2) clustering technique and the decision is declared as:

i. Find the centroids for $\sigma_{\{brady,normal,tachy\}}$ outcome set as $\mathcal{C} = \mathcal{C}_{\{brady,normal,tachy\},i=1,2}$ ii. Decision $\mathcal{D} = \min\{\mathcal{C}\}$ In an exemplary embodiment of the present invention, in the data taken from publicly available MIT-Physionet challenge 2015, for patient #t114s, it is computed that $\mathcal{D} = \mathcal{C}$ and declared the patient is suffering from tachycardia.

In another embodiment of the present invention, the following method is implemented to determine the detection of asystole:

a. Find peak-to-peak interval in seconds for PPG signal: $\rho_{PPG}=\psi_k \times 60$, $\forall k \in (K-2)$.

b. If ($\{\exists \rho_{PPG}>4\}$), Declare 'Asystole'.

In another embodiment of the present invention, the following method is implemented to determine the detection of ventricular tachycardia:

a. Find longest peak-to-peak interval in seconds for PPG signal as $\rho_{PPG}|_{longest}$, $\rho_{PPG}|_{shortest}$ respectively.

b. If, $\{(\mathcal{H} \geq 5) \wedge (\rho_{PPG}|_{longest}>1.8) \vee (\rho_{PPG}|_{shortest} \times 60>80)\}$, Declare 'Ventricular Tachycardia'.

In another embodiment of the present invention, the following method is implemented to determine the detection of ventricular flutter:

a. If $\{(\mathcal{H} \geq 0.5) \wedge (\rho_{PPG}|_{longest}>1.8) \vee (\rho_{PPG}|_{shortest} \times 60<150)\}$, Declare 'Ventricular Flutter', where H=Hurst exponent In an exemplary embodiment of the present invention, for demonstrating the efficacy of the present invention, 750 patients' cardio-signals sampled at 250 Hz from the data taken from the publicly available MIT-Physionet challenge 2015 with expert annotations are considered. The prediction problem is evaluated by confusion matrix parameters: False Positives (FP), False Negatives (FN), True Positives (TP) and True Negatives (TN) and are shown in the tables below.

Extereme Ventricular Tachycardia Detection Performance

|  | Predicted (Yes) | Predicted (No) |
|---|---|---|
| Actual (Yes) | TP = 89% | FN = 4% |
| Actual (No) | FP = 3% | TN = 4% |

| ACCURACY | SPECIFICITY | SENSITIVITY | PRECISION |
|---|---|---|---|
| 93% | 57% | 96% | 97% |

Bradycardia Detection Performance

|  | Predicted (Yes) | Predicted (No) |
|---|---|---|
| Actual (Yes) | TP = 52% | FN = 0% |
| Actual (No) | FP = 29% | TN = 19% |

| ACCURACY | SPECIFICITY | SENSITIVITY | PRECISION |
|---|---|---|---|
| 71% | 40% | 100% | 64% |

Asystole Detection Performance

|  | Predicted (Yes) | Predicted (No) |
|---|---|---|
| Actual (Yes) | TP = 15% | FN = 3% |
| Actual (No) | FP = 40% | TN = 42% |

| ACCURACY | SPECIFICITY | SENSITIVITY | PRECISION |
|---|---|---|---|
| 57% | 51% | 83% | 27% |

Premature Ventricular Contraction Detection Performance

|  | Predicted (Yes) | Predicted (No) |
|---|---|---|
| Actual (Yes) | TP = 24% | FN = 2% |
| Actual (No) | FP = 54% | TN = 20% |

| ACCURACY | SPECIFICITY | SENSITIVITY | PRECISION |
|---|---|---|---|
| 44% | 27% | 92% | 31% |

Ventricular Flutter Detection Performance

|  | Predicted (Yes) | Predicted (No) |
| --- | --- | --- |
| Actual (Yes) | TP = 9% | FN = 2% |
| Actual (No) | FP = 47% | TN = 42% |

| ACCURACY | SPECIFICITY | SENSITIVITY | PRECISION |
| --- | --- | --- | --- |
| 51% | 47% | 82% | 16% |

It is observed from the data in tables above that, false negatives from the invention's experimental results are have consistently proven to be very low (below 4%), which significantly decreases the number of undetected conditions. It is to be noted that asystole and ventricular fibrillation condition detection is subjective and expert opinion often differs. However, both of the arrhythmia conditions being fatal condition, false negative are extremely important for the purpose.

In another embodiment of the present invention, classification of type of arrhythmia comprises of classifying into critical and non-critical, wherein the non-critical type of arrhythmia is selected from a group comprising of bradycardia and extreme ventricular tachycardia and critical type of arrhythmia is selected from a group comprising of premature ventricular contraction, ventricular flutter and asystole.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A method of detecting arrhythmia using photoplethysmogram (PPG) signal, said method comprising:
   extracting photoplethysmogram (PPG) signals by a mobile communication device (204) from an image capturing device (202) coupled with the mobile communication device (204);
   extracting cardiac parameter from the extracted photoplethysmogram (PPG) signals using a feature extraction module (206), wherein the extracted cardiac parameter is heart rate;
   identifying presence of cardiac abnormalities as reinforcement filtering of detecting premature ventricular contraction and ventricular flutter from the extracted cardiac parameters using an abnormality detection module (208);
   analysing the extracted cardiac parameters to investigate statistical trend and to perform statistical closeness approximation of the extracted photoplethysmogram (PPG) signals using a closeness criteria evaluation module (210); and
   predicting and subsequently classifying type of arrhythmia using a decision module (212),
   wherein the analysing, predicting and subsequently classifying type of arrhythmia based on the extracted cardiac parameters comprises:
      finding train of heart rates at each cardiac cycle for given PPG signal;
      finding feature vector from mean heart rate values;
      finding the classification outcome set from the heart rate values using binary classifier k-means clustering technique; and
      deciding the type of arrhythmia based on the classification.

2. The method according to claim 1, wherein the photoplethysmogram (PPG) signals are extracted from a user's peripheral body parts.

3. The method according to claim 2, wherein the user's peripheral body parts are selected from a group comprising of fingertip, ear, toe; and forehead.

4. The method according to claim 1, wherein the photoplethysmogram (PPG) signals are extracted from a user using a light emitting source attached to the image capturing device (202) coupled with the mobile communication device (204).

5. The method according to claim 1, wherein the image capturing device (202) coupled with the mobile communication device (204) extracts photoplethysmogram signals (PPG) as a video stream.

6. The method according to claim 1, wherein the extraction of cardiac parameter is performed using signal processing technique.

7. The method according to claim 1, wherein the identification of presence of abnormalities in the extracted photoplethysmogram (PPG) signals is performed by calculating Hurst exponent of the stream of heart rates derived from the extracted PPG signal as reinforcement filtering of detecting premature ventricular contraction and ventricular flutter.

8. The method according to claim 1, wherein the analysis of the cardiac parameters to investigate statistical trend and to perform statistical closeness approximation from the extracted photoplethysmogram (PPG) signals is performed to evaluate morphological trend.

9. The method according to claim 1, wherein the classification of type of arrhythmia is based on the statistical trend investigation and the performed statistical closeness approximation.

10. The method according to claim 1, wherein the classification of type of arrhythmia comprises of classifying into critical and non-critical.

11. The method according to claim 10, wherein the critical type of arrhythmia is selected from a group comprising of premature ventricular contraction, ventricular flutter and asystole.

12. The method as claimed in claim 10, wherein the non-critical type of arrhythmia is selected from a group comprising of bradycardia and extreme ventricular tachycardia.

13. A system of detecting arrhythmia using photoplethysmogram (PPG) signals; said system comprising:
   an image capturing device (202) coupled with a mobile communication device (204), adapted for extracting photoplethysmogram signals from a patient;
   a feature extraction module (206) adapted for extracting cardiac parameter from the extracted photoplethysmogram (PPG) signals), wherein the extracted cardiac parameter is heart rate;
   an abnormality detection module (208) adapted for identifying presence of cardiac abnormalities as reinforcement filtering of detecting premature ventricular contraction and ventricular flutter from the extracted cardiac parameters;
   a closeness criteria evaluation module (210) adapted for analysing the extracted cardiac parameters to investigate statistical trend and to perform statistical closeness approximation of the extracted photoplethysmogram (PPG) signals;
   a decision module (212) adapted for predicting and subsequently classifying type of arrhythmia,
   wherein the analysing, predicting and subsequently classifying type of arrhythmia based on the extracted cardiac parameters comprises:
      finding train of heart rates at each cardiac cycle for given PPG signal;
      finding feature vector from mean heart rate values;
      finding the classification outcome set from the heart rate values using binary classifier k-means clustering technique; and
      deciding the type of arrhythmia based on the classification.

14. A non-transitory computer readable medium storing instructions which when executed by a possessor on a system, cause the processor to perform method for detecting arrhythmia using photoplethysmogram (PPG) signals comprising:
   extracting photoplethysmogram (PPG) signals by a mobile communication device from an image capturing device (202) coupled with the mobile communication device (204);
   extracting cardiac parameter from the extracted photoplethysmogram (PPG) signals using a feature extraction module (206)), wherein the extracted cardiac parameter is heart rate;
   identifying presence of cardiac abnormalities as reinforcement filtering of detecting premature ventricular contraction and ventricular flutter from the extracted cardiac parameters using an abnormality detection module (208);
   analysing the extracted cardiac parameters to investigate statistical trend and to perform statistical closeness approximation of the extracted photoplethysmogram (PPG) signals using a closeness criteria evaluation module (210); and
   predicting and subsequently classifying type of arrhythmia using a decision module (212),
   wherein the analysing, predicting and subsequently classifying type of arrhythmia based on the extracted cardiac parameters comprises:
      finding train of heart rates at each cardiac cycle for given PPG signal;
      finding feature vector from mean heart rate values;
      finding the classification outcome set from the heart rate values using binary classifier k-means clustering technique; and
      deciding the type of arrhythmia based on the classification.

* * * * *